United States Patent [19]
Witte et al.

[11] Patent Number: 5,446,065
[45] Date of Patent: Aug. 29, 1995

[54] SULFONAMIDES OF PHENYLALKYLAMINES OR PHENOXYALKYLAMINES PROCESSES FOR THEIR PREPARATION AND MEDICAMENTS CONTAINING THESE COMPOUNDS

[75] Inventors: Ernst-Christian Witte, Mannheim; Hansjorg Beckh, Burstadt; Karlheinz Stegmeier, Heppenheim; Liesel Doerge, Lampertheim, all of Germany

[73] Assignee: Boehringer Mannheim GmbH, Mannheim, Germany

[21] Appl. No.: 75,489

[22] PCT Filed: Dec. 19, 1991

[86] PCT No.: PCT/EP91/02456

§ 371 Date: Jun. 21, 1993

§ 102(e) Date: Jun. 21, 1993

[87] PCT Pub. No.: WO92/11234

PCT Pub. Date: Jul. 9, 1992

[30] Foreign Application Priority Data

Dec. 24, 1990 [DE] Germany ............ 40 41 780.8

[51] Int. Cl.⁶ ............................................. A61K 31/18
[52] U.S. Cl. ........................................ 514/604; 514/331; 514/352; 514/357; 514/398; 514/400; 514/406; 514/411; 514/416; 514/538; 514/548; 514/562; 514/564; 514/602; 546/232; 546/309; 546/312; 548/340.1; 548/371.7; 548/444; 548/470; 548/558
[58] Field of Search .............. 564/92, 90, 93; 514/604, 331, 352, 357, 398, 400, 406, 411, 416, 538, 540, 562, 564, 602; 546/232, 309, 312; 548/340.1, 371.7, 444, 470, 558; 562/556

[56] References Cited

U.S. PATENT DOCUMENTS

| | | | |
|---|---|---|---|
| 4,122,255 | 10/1978 | Krapcho | 542/421 |
| 4,127,606 | 11/1978 | Krapcho | 260/556 A |
| 4,258,058 | 3/1981 | Witte et al. | 424/309 |
| 4,539,426 | 9/1985 | Buzby, Jr. | 564/92 |
| 4,948,810 | 8/1990 | Iwakuma et al. | 514/539 |

OTHER PUBLICATIONS

Umino et al., *Tetrahedron Letters*, 10: 763-66 (1976).

*Primary Examiner*—Allen J. Robinson
*Assistant Examiner*—Brian M. Burn
*Attorney, Agent, or Firm*—Nikaido, Marmelstein, Murray & Oram

[57] ABSTRACT

Compounds of the formula I

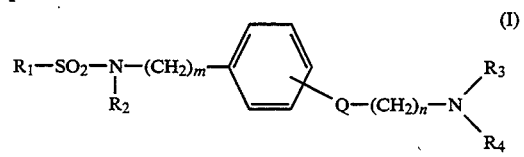

in which $R_1$ signifies an aryl, aralkyl or an aralkenyl group, the aryl radical of which can, in each case, be substituted one or more times by halogen, cyano, alkyl, trifluoromethyl, alkoxy, alkylthio, trifluoromethoxy, hydroxyl or carboxyl, m a whole number from 1 to 3, n a whole number from 1 to 5, $R_2$ hydrogen, an alkyl, aralkyl or acyl group, Q a bond or an oxygen atom, $R_3$ hydrogen or a lower alkyl radical which is possibly terminally substituted by carboxyl or by a hydroxyl group and $R_4$ hydrogen, a lower alkyl group with 1-4 C-atoms, which is possibly terminally substituted by carboxyl or hydroxyl, a possibly substituted phenyl, heteroaryl, cycloalkyl or acyl group or a group

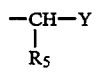

in which $R_5$ represents a straight-chained or branched alkyl chain with 1-4 C-atoms which is possibly terminally substituted by carboxyl, alkoxycarbonyl, aminocarbonyl, hydroxyl, mercapto, alkylthio or imidazolyl and Y a carboxyl, an alkoxycarbonyl, aminocarbonyl or cyano, formyl, hydroxymethyl, aminomethyl or ortho ester group, whereby $R_3$ and $R_4$ can also be component of a 5- or 6-membered saturated or unsaturated possibly substituted heterocycle with 1-4 heteroatoms which can be annellated with further ring compounds via one or more bonds, as well as their salts, esters and amides, processes for their preparation and medicaments with thromboxane-antagonistic action which contain these compounds.

15 Claims, No Drawings

SULFONAMIDES OF PHENYLALKYLAMINES OR PHENOXYALKYLAMINES PROCESSES FOR THEIR PREPARATION AND MEDICAMENTS CONTAINING THESE COMPOUNDS

The present invention concerns new amines of the general formula I

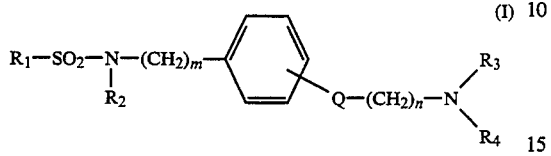

in which $R_1$ signifies an aryl, aralkyl or an aralkenyl group, the aryl radical of which can be substituted one or more times by halogen, cyano, alkyl, trifluoromethyl, alkoxy, alkylthio, trifluoromethoxy, hydroxyl or carboxyl, m a whole from 1 to 3, n a whole number from 1 to 5, $R_2$ hydrogen, an alkyl, aralkyl or acyl group, Q a bond or an oxygen atom, $R_3$ hydrogen or a lower alkyl group which is possibly terminally substituted by carboxyl or by a hydroxyl group and $R_4$ hydrogen, a lower alkyl group with 1-4 C-atoms, which is possibly terminally substituted by carboxyl or hydroxyl, a possibly substituted phenyl, heteroaryl, cycloalkyl or acyl group or a group

in which $R_5$ represents a straight-chained or branched alkyl chain with 1-4 C-atoms, which is possibly terminally substituted by carboxyl, alkoxycarbonyl, aminocarbonyl, hydroxyl, mercapto, alkylthio or imidazolyl, and Y a carboxyl, an alkoxycarbonyl, aminocarbonyl or cyano, formyl, hydroxymethyl, aminomethyl or an ortho ester group, whereby $R_3$ and $R_4$ can also be component of a 5- or 6-membered saturated or unsaturated possibly substituted heterocycle with 1-4 heteroatoms which can be annellated with further ring compounds via one or more bonds.

Thus, the subject of the invention are sulphonamide group-containing phenylalkylamines and phenoxyalkylamines.

The invention includes compounds of the general formula I in which the sulphonamidoalkyl radical stands not only in ortho but also in meta or para position to the radical —Q—(CH$_2$)$_2$—NR$_3$R$_4$. The meta and the para position are especially preferred.

If the compounds of the general formula I contain asymmetric carbon atoms, then not only the pure optical isomers (enantiomers) but also their mixture/racemates are contained in the claim.

For the case that the compounds I contain carboxyl groups, their physiologically acceptable salts, esters and amides are also claimed.

Such compounds have hitherto not been described. There are only two publications concerning disulphonamides of the phenylalkylamine type: D. B. Baird et al. Soc. Perkin Trans. 1, No. 8 (1973), 832 and J. H. Wood and R. E. Gibson, Am. Soc. 71 (1949), 393. In neither of the two cited works is a pharmacological action described.

The subject of previous patents/publications were only sulphonamide group-containing phenoxycarboxylic acids, as well as their esters and amides, furthermore phenylalkylcarboxylic acids, as well as their esters and amides, phenoxyalkylcarboxylic acid amides with amino acids as amine component, as well as sulphonamide group-containing tetrazole compounds. In principle, all these compounds contain an acid function. Therefore, it was surprising that the acid function can be replaced by a basic amine function without therein being observed a loss of the pharmacological activity observed in the case of the acid compounds.

The new compounds of the general formula I show an excellent antagonistic action towards thromboxane $A_2$, as well as against prostaglandin endoperoxides. They inhibit the activation of blood platelets and of other blood cells and prevent the constriction of the smooth musculature of bronchi and blood vessels, as well as the contraction of mesangium cells and of similar cells with contractile properties.

This action makes them valuable remedies for the treatment of cardiovascular diseases, such as acute heart and brain infarct, cerebral and coronary ischaemia, migraine, peripheral arterial occlusive diseases, as well as venous and arterial thromboses. Furthermore, their early use can favourably influence the appearance of organ damages in the case of shock patients. Furthermore, they are suitable for the prevention of thrombocyte and leukocyte depositions in the case of interventions with an extracorporeal circulation and in the case of haemodialysis. Their addition to thrombocyte concentrates stabilises the blood platelets and thus increases the storability of the preserves.

Since, in the case of bronchial asthma, thromboxane is a mediator of the inflammatory reaction, by means of the use of these thromboxane receptor blockers, in particular the hyperreactivity characteristic for chronic asthma can be mitigated or even overcome.

Furthermore, the new thromboxane receptor blockers are protectively active in the case of gastritis and tendency to ulceration and can thus be used for recidive prophylaxis. In a model of experimental acute pancreatitis, the course thereof could be improved by the use of a thromboxane antagonist. It is thus to be expected that at least certain forms of acute pancreatitis in humans can be improved in their prognosis by the use of these thromboxane antagonists.

In addition, these new compounds are able to inhibit the acetate incorporation into cholesterol and are, therefore, suitable also for the treatment of fat metabolism diseases which involve an increased cholesterol synthesis. Especially to be stressed is their outstanding anti-atherogenic effect in the case of increased cholesterol values which manifests itself in a reduction of the plaque formation, especially in the coronary arteries and in the aorta.

Since diabetes involves an increased formation of thromboxane, by means of the chronic use of these thromboxane antagonists, the typical late damages of blood vessels of the kidneys and in the eye can be delayed or even prevented in their development.

Also in the case of a series of immunologically- or non-immunologically-caused kidney diseases, such as e.g. glomerulonephritis, acute kidney failure, transplant rejection and kidney damage caused by nephrotic substances, an increased excretion of thromboxane B2 in the urine was observed. In the case of these diseases, an intervention with the new thromboxane antagonists promises success with regard to the maintenance of the kidney function.

Since, in the case of tumour cells, an incressed thromboxane synthesis has been demonstrated and, at the same time, the proliferation of these cells could be inhibited by the administration of thromboxane antagonists, these represent an effective adjuvant therapy.

In the case of pathological pregnancy, a disturbance of the equilibrium of the prostaglandins is regarded as causative. Therefore, by means of blockade of the thromboxane and PGF2 alpha receptors, especially the premature labour pains can be interrupted and, in the case of pregnancy gestosis or eclampsia, a more favourable course can be achieved. In addition, the prostaglandin-caused symptoms of of dysmenorrhoea and of the premenstrual syndrome can hereby also be treated therapeutically.

As aryl radical $R_1$, alone or in combination with an alkyl or alkenyl chain, there are, in all cases, to be understood aromatic hydrocarbons with 6–14 C-atoms, especially the phenyl, the biphenylyl, the naphthyl and the fluorenyl radical. These aryl radicals can be substituted one, two or three times in all possible positions, whereby, as substituents, halogen, $C_1$–$C_6$-alkyl, $C_1$–$C_6$-alkoxy, $C_1$–$C_6$-alkylthio, trifluoromethoxy, hydroxyl, carboxyl, trifluoromethyl or cyano come into question. The phenyl radical is preferred which can be substituted by halogen (preferably chlorine or bromine), methoxy, methyl or trifluoromethyl.

As aralkyl radicals $R_1$, those come into question the straight-chained or branched alkylene part of which contains 1–5 carbon atoms. Preferred aralkyl radicals $R_1$ are the phenethyl and the 4-chlorophenethyl radical.

Amongst aralkenyl radicals $R_1$ are to be understood those, the alkenylene part of which contains 2–3 carbon stems. The styryl and the 4-chlorostyryl radical are here preferred.

Amongst the alkyl, alkoxy and alkylthio substituents of the aryl, aralkyl and aralkenyl radicals, radicals are preferred with 1–4 C-atoms, especially the methyl, ethyl, isobutyl and tert.-butyl groups, as well as the methoxy and methylthio group.

By halogen is, in all cases, to be understood fluorine, chlorine and bromine.

As alkyl groups $R_2$, there come into question straight-chained or branched ones with 1–16 C-atoms, the groups methyl and octyl being preferred.

As aralkyl radicals $R_2$, those come into question in which the aryl radical represents a phenyl or a 4-chlorophenyl group and the alkyl part consists of 1 to 2 carbon atoms. The 4-chlorobenzyl and the 4-chlorophenethyl radical are preferred.

The acyl radicals $R_2$ are derived from aliphatic carboxylic acids with 2–16 C-atoms, from araliphatic and from aromatic carboxylic acids. Preferred acyl groups are acetyl, isobutyroyl, cinnamoyl, benzoyl, 4-chlorobenzoyl and 4-aminobenzoyl, as well as n-octanoyl and n-hexadecanoyl.

m preferably signifies the number 2, whereas for n the numbers 1 to 4 are preferred.

$R_3$ preferably means hydrogen or an alkyl group with 1–4 C-atoms which is terminally substituted by a carboxyl group or a hydroxyl group. The preferred hydroxyalkyl group is the hydroxyethyl group.

$R_4$ preferably signifies a hydrogen atom or a $C_1$–$C_4$-alkyl group which is possibly terminally substituted by carboxyl or hydroxyl. In the latter case, the hydroxyethyl group is here also preferred. If $R_4$ signifies a phenyl radical, then the unsubstituted phenyl radical or the one substituted by one or two chlorine atoms are especially preferred. Heteroaryl signifies a 5- or 6-membered ring with one or more heteroatoms, whereby the atoms O, N, S, SO or $SO_2$ are to be understood hereunder. The following radicals are, for example, especially preferred: pyridine which is attached in the 2-, 3- or 4-position with the nitrogen stores of the $-NR_3R_4$ group, furthermore the 1,2,4-triazine, pyridazine, pyrazole, pyrazine, pyrimidine, 1H-1,2,4-triazole, thiazole and the 1,3,4-thiadiazole radical. The heterocycles can possibly be linked with $C_1$–$C_6$-alkyl, $C_1$–$C_6$-acyl, phenyl, halogen, cyano or carboxyl substituents. The cyclopentyl and the cyclohexyl radical count are especially preferred cycloalkyl radicals. As preferred acyl radicals, those defined under $R_2$ also count here.

If $R_4$ signifies a group

then $R_5$ preferably signifies a hydrogen atom or an unbranched or branched-alkyl chain with 1–4 C-atoms which is possibly terminally substituted. As preferred substituents, there are to be mentioned: carboxyl, aminocarbonyl, mono- and di-$C_1$–$C_6$-alkylaminocarbonyl, $C_1$–$C_6$-alkoxycarbonyl, $C_1$–$C_6$-alkylthio, phenylthio, hydroxyl, phenyl and 4-imidazolyl.

Y preferably signifies a carboxyl group but can also signify a $C_1$–$C_6$-alkoxycarbonyl, aminocarbonyl, cyano, formyl, hydroxymethyl, aminomethyl or an ortho ester group.

Quite especially preferred are those compounds I in which Y=COOH and in which $R_3$ and $R_5$, together with Y=COOH, give the structure of an essential amino acid. To these belong all possible isomers and their mixtures/racemates.

To the amino acids belong especially alanine, arginine, asparagine, aspartic acid, cysteine, cystine, glutamine, glutamic acid, glycine, histidine, isoleucine, leucine, lysine, methionine, phenylalanine, proline, serine, threonine, tryptophane, tyrosine, valine, homocysteine, homoserine, hydroxylysine, hydroxyproline, ornithine, sarcosine, norvaline or 2-aminobutyric acid.

If R3 and R4 are components of a 5- or 6-membered saturated or unsaturated heterocycle with one or more heteroatoms, then for the group

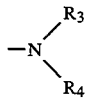

there come into question ring compounds which are attached via a nitrogen atom with the alkyl chain Q—$(CH_2)_n$— in formula I.

As saturated rings, there preferably come into consideration pyrrolidine, piperidine, morpholine, thiomorpholine, 1,1-dioxothiomorpholine, piperazine, piperazine substituted on the nitrogen by an alkyl, aralkyl or aryl group.

As unsaturated ring compounds, there preferably come into question pyrrole, pyrazole and imidazole, as well as benz-annellated compounds, such as indole, carbazole or compounds of the purine type.

Preferred are compounds of the formula I in which $R_1$ is 4-chlorophenol, 4-methylphenyl, 4-methoxyphenyl or 4-trifluoromethylphenyl, $R_2$ hydrogen, m the number 2, Q a bond or oxygen, n the number 1, 2, 3 or 4, $R_3$ hydrogen, $R_4$ phenyl, cyclohexyl, pyridyl, pyrazolyl or the radical

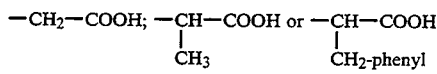

or $R_3$ and $R_4$, together with the nitrogen atom, form a piperidine, piperazine, morpholine, pyrrole, imidazole, pyrazole, indole or carbazole ring.

For the case that the compounds of the general formula I contain a carboxyl function, as esters of these carboxylic acids those come into question with lower monohydroxy alcohols (such as e.g. methanol or ethanol) or with polyhydroxy alcohols (such as e.g. glycerol) but also those alcohols are included which contain still other functional groups, such as e.g. ethanolamine.

As amides of these carboxylic acids, those are claimed in which the amine component is e.g. ammonia, a lower dialkylamine, such as e.g. diethylamine, or a hydroxyalkylamine, such as e.g. ethanolamine or diethanolamine. Other claimed amine components are alkyl-, aralkyl- and arylpiperazines.

The subject of the invention are also the new carbonamides of the gen. formula II to be used as starting material for the process a). Compounds II in which $-NR_3R_4$ has the meaning of an amino acid, thus in which $R_3=H$ and $R_4=-CH(R_5)-Y$, are described in the Application DE-A-5942923.7. Furthermore, the following mentioned compounds are described in EP-A-4011:

1) 4-[2-(benzoylsulphonamido)-ethyl]-phenylacetic acid [4-methylpiperazide]
2) 4-[2-(benzenesulphonamido)-ethyl]-phenoxyacetamide
3) 4-[2-(benzenesulphonamido)-ethyl]-phenoxyacetic acid (1-hydroxy-2-propylamide)
4) 4-[2-(benzenesulphonamido)-ethyl]-phenoxyacetic acid (2-carboxyethylamide)
5) 4-[2-(benzenesulphonamido)-ethyl]-phenoxyacetanilide and
6) 4-[2-(benzenesulphonamido)-ethyl]-phenoxyacetic acid (4-carboxyanilide).

The new carbonamides of the formula II are prepared according to per se known processes from the appropriate carboxylic acid or a reactive derivative thereof by reaction with the appropriate amines.

The preparation of the new amines of the general formula I is characterised in that one a) reduces a carboxylic acid amide of the general formula II

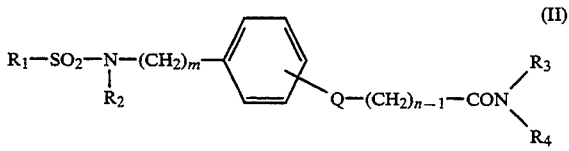

in which $R_1$, $R_2$, $R_3$, $R_4$, Q, m and n have the above-given meaning, to the amine, or b) instead of carbonamides according to a), reduces other functions containing a nitrogen atom:

1. azides III

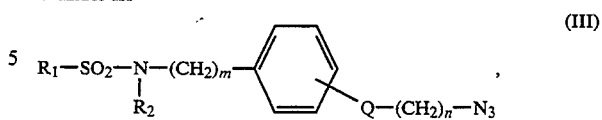

2. nitroalkanes IV

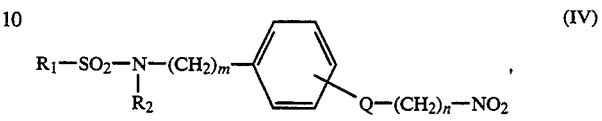

3. nitriles V

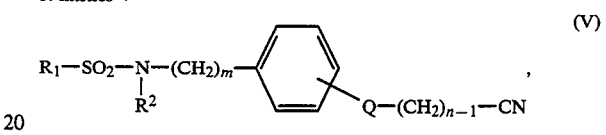

4. oximes VI

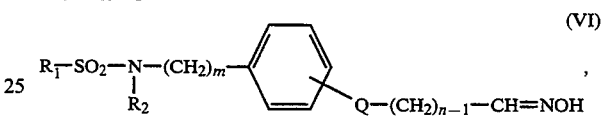

whereby, in each case, <u>primary</u> amines (I, $R_3 = R_4 = H$) are formed, or 5. Schiff's bases VII

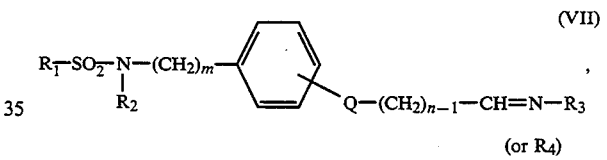

(or $R_4$)

whereby secondary amines are formed, or c) reacts a compound of the general formula VIII

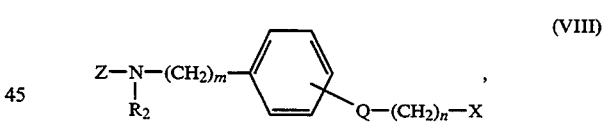

in which $R_2$, Q, m and n have the above-given meaning, Z represents a protective group for the amine function and X a reactive group, in per se known manner first with a possibly optically-active compound of the general formula IX

($R_5$ and $R_4$ here also have the above-given meaning) and then, after splitting off the protective group Z, with a sulphonic acid of the general formula X

or with a derivative thereof, or d) brings a compound of the general formula XI

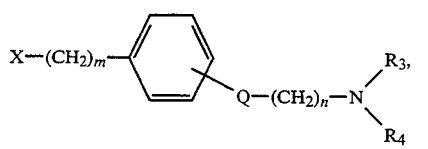  (XI)

to reaction with a sulphonamide of the general formula XII

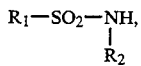  (XII)

whereby $R_1$, $R_2$, $R_3$, $R_4$, X, Q, m and n have the above-given meaning, or, for the case that Q=oxygen, e) reacts an amine of the general formula XIII

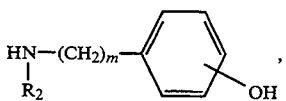  (XIII)

in which $R_2$ and m have the above-given meaning, possibly with intermediate protection of the amino or hydroxyl group, respectively, in per se known manner in any desired sequence with a sulphonic acid of gen. formula X or a derivative thereof and with possibly optically-active compound of the general formula XIV

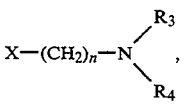  (XIV)

whereby X, n, $R_3$ and $R_4$ have the above-given meaning.

f) As special process for the preparation of primary amines (I, $R_3=R_4=H$), there is to be mentioned the Delepine reaction which consists of the reaction of a compound of the formula XV

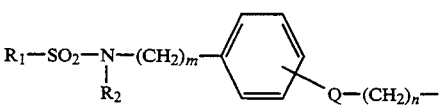  (XV)

in which $R_1$, $R_2$, m, n, Q and X have the above-given meaning, with hexamethylenetetramine to give a quaternary ammonium salt and subsequent hydrolysis.

g) One also obtains primary amines (I, $R_3=R_4=H$; Q=bond) by Hofmann decomposition of carboxylic acid amides XVI

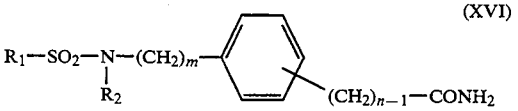  (XVI)

by means of alkali metal hypobromite.

h) As a special process for the preparation of primary phenethylamines (I, Q=bond, n=2, $R_3=R_4=H$), there is to be mentioned the reduction of nitrostyrenes XVII

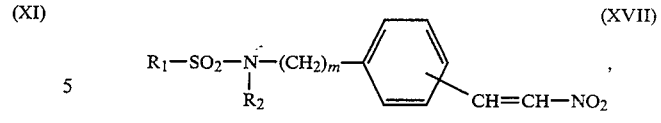  (XVII)

i) One obtains primary amines in that, in process a), instead of II, one uses a protected carbonamide of the general formula IIa

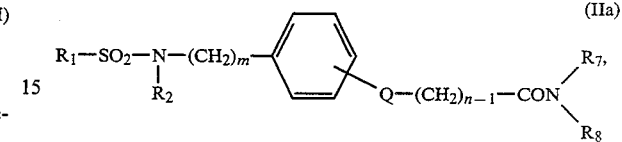  (IIa)

wherein $R_1$, $R_2$, m, Q and n have the above-given meanings, $R_7=H$, $R_8=$a protective group or $R_7$ and $R_8$ together signify a protective group, and, after reduction has taken place, removes the protective group.

j) One also obtains primary amines in that, in process e), instead of XIV, one uses a protected amine of the general formula XIVa

  (XIVa)

wherein X, n, $R_7$ and $R_8$ have the above-given meaning, and subsequently removes the protective group.

For the reduction of the carbonamides according to process a) or of the azides, nitro and cyano compounds, oximes and Schiff's bases according to process b), there can, in principle, be used all processes known from the literature for the groups in question. As reducing agents, there can be used: complex boron and aluminium hydrides, boron hydride complexes, aluminium hydride ($LiAlH_4+AlCl_3$), a mixture of $AlCl_3$ and $NaBH_4$, hydrogen in statu nascendi (alcohol+sodium), as well as catalytically activated hydrogen, possibly under pressure. If the carbonamides II to be reduced contain those groups $R_3$ or $R_4$ which would also be changed with strong reducing agents (e.g. alkoxycarbonoyl), then one first converts the carbonamide with $PCl_5$ into a "Vilsmeier complex" and then reduces this with a mild-acting reducing agent, such as sodium borohydride or zinc to ethanol.

However, with $NaBH_4$, a partial reduction of the alkoxycarbonyl group to the alcohol function takes place more frequently.

The mentioned reduction processes also apply to the case that, according to i), one wishes to reduce protected carbonamides.

The starting compounds used in the case of process b) are in part novel and can be obtained by per se known processes from corresponding alcohols or aldehyde. Some of the nitriles of the formula II are e.g. partly described in EP-A-556 989 and can be prepared by the given processes.

The reactions of a compound of the general formula VIII with an amine of gen. formula IX (i.e. process c) expediently takes place in such a manner that one first blocks the amino group of a compound of gen. formula XVIII

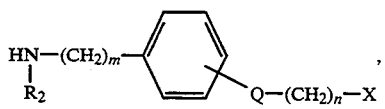

(XVIII)

in which $R_2$, m, Q, n and X have the above-given meaning, with a protective group which can easily be split off again so that a compound VIII results. Especially suitable are here the protective groups known from peptide chemistry which can easily be removed by hydrogenation or by acid hydrolysis, such as e.g. the benzyloxycarbonyl group. Also suitable are protective groups such as the phthalimido group which, after condensation has taken place between VIII and IX, can easily be split off again, e.g. by means of hydroxylamine. Sometimes, one can completely omit the splitting off in that, from the very beginning, one introduces the group $R_1-SO_2-$. As reactive groups X of the compounds VIII (as well as also all following X-containing compounds), those especially come into question in which X represents a halogen atom or an alkylsulphonyloxy or arylsulphonyloxy group. The reaction of a compound VIII with a compound IX expediently takes place in inert solvents, such as e.g. toluene or methylene chloride, whereby, as acid acceptor, one expediently adds an excess of a tert.-amine, such as e.g. pyridine or triethylamine.

The splitting off of the protective group takes place according to processes such as are known from the peptide chemistry literature. Thus, the benzyloxycarbonyl radical can be split off e.g. by catalytic hydrogenation but also by acid hydrolysis, e.g. with aqueous HBr solution. The compounds resulting therefrom of the general formula XIX

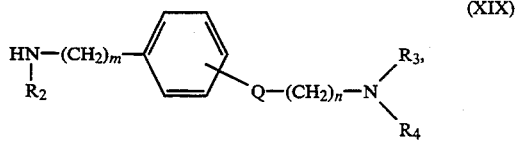

(XIX)

in which $R_2$, $R_3$, $R_4$, m, n and Q have the above-given meaning, are now converted into sulphonamides. As reactive derivatives of the sulphonic acids X, there come into consideration especially their halides, as well as their esters. The reactions of the sulphonic acid chlorides preferably employed with the compounds XIX expediently takes place with the addition of an acid-binding agent, such as e.g. alkali metal acetate, alkali metal carbonate, alkali metal hydrogen carbonate, sodium phosphate, alkali metal hydroxide, calcium oxide, calcium carbonate or magnesium carbonate. However, this function can also be undertaken by organic bases, such as e.g. pyridine or triethylamine, whereby, as inert solvent, there serves e.g. ether, methylene chloride, dioxane, toluene or an excess of the tertiary amine. In the case of the use of inorganic acid binders, as reaction medium one uses e.g. water, aqueous ethanol or aqueous dioxane.

For the reaction described under d) between a compound XI with a sulphonamide XII, it has proved to be especially preferable to react a primary sulphonamide XII, $R_2=H$, first by reaction with e.g. hexamethyldisilazine to give the trimethylsilyl sulphonamide XII, here $R_2=-SiMe_3$. Its reaction with XI gives a product which is free from disubstituted sulphonamide. Another way makes use of the alkali metal salts of the sulphonamides XII: Two mol of sulphonamide XII are evaporated to dryness with one mol of alcoholic sodium alcoholate solution. The mixture obtained is now reacted with one mol of a compound XI. In this way, too, the condensation of the sulphonamide with two mol of XI is prevented.

One expediently carries out the process sketched out under e) in two steps. The condensation of the compounds of the general formula XIII with sulphonic acids (X) or with their derivatives, on the one hand, and compounds of the general formula XIV, on the other hand, is preferably so carried out that one first blocks one of the two reactive groups of the compound XIII with a protective group which can easily be split off, reacts the compound obtained with a sulphonic acid (X) or a derivative thereof or with a compound of the general formula XIV, again splits off the protective group and subsequently reacts this reactive intermediate product with the not yet used compound of the general formula XIV or (X), respectively. A process is preferred in which the compound XIII protected on the amino group (i.e. the compound XX) is first brought to reaction with a compound XIV. After splitting off the protective group, there then takes place the reaction with a sulphonic acid (X) or with one of its derivatives:

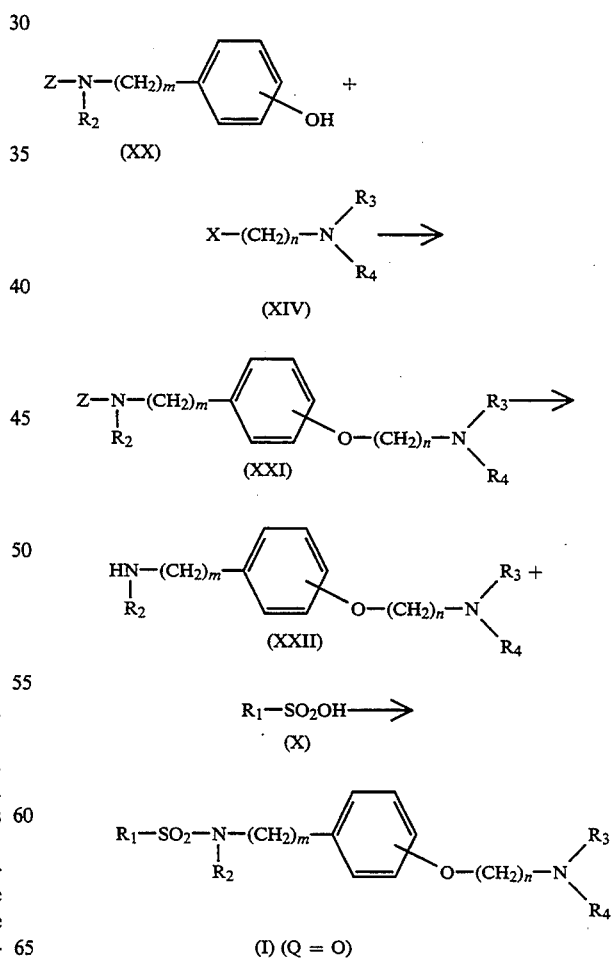

(I) (Q = O)

The symbols used in the above-given formulae have the already given meaning.

An analogous process is used when one wishes to get to those compounds I, Q=O, which are to be subsequently modified on the amino group: Instead of XIV, one reacts a compound of the general formula XIVa

in which X, n and $R_7$, $R_8$ have the meaning given in j), with a compound XX, obtains a compound XXIa (in which the substituents $R_3$ and $R_4$ of the compound XXI are replaced by $R_7$, $R_8$), removes the protective group Z (whereby XXIIa results) and, after reaction with a sulphonic acid X, obtains a compound Ia, Q=O:

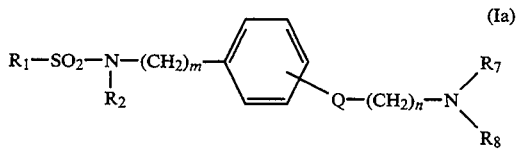

After removal of the protective group $R_7$ or $R_7$, $R_8$, this compound can be used for numerous conversions of the amino group ($R_7$, $R_8$=H).

The reaction of a phenol XX with an activated compound XIV or XIVa is expediently so carried out that the phenol is used in the form of its sodium or potassium salt. As reaction medium, there serve solvents, such as e.g. toluene, methyl ethyl ketone, dimethylformamide or dimethyl sulphoxide.

The possible subsequent N-alkylation of a compound of the general formula I, in which $R_2$= hydrogen, can be carried out according to known methods, preferably in that one reacts it with an alkyl halide or a dialkyl sulphate in the presence of an acid-binding agent, such as e.g. potassium carbonate. For the case that $R_3$ and/or $R_4$ signify a hydrogen atom, these hydrogen atoms must be intermediarily replaced by a protective group. As protective groups, there here also serve those known from peptide chemistry, e.g. the benzyloxycarbonyl group, or $NR_3R_4$ means e.g. a phthalimido group.

The same applies for the case that $R_2$ represents an acyl radical. Here, too, the subsequent acylation of a compound of the formula I, in which $R_2$=H and $R_3$ and/or $R_4$ possibly signifies a protective group, is preferred.

The introduction of an acyl group $R_2$ into a sulphonamide of the general formula (I)($R_2$=H) takes place under conditions such as are usual for the acylation of amines: reaction with an active carboxylic acid derivative, e.g. an acid halide, a mixed anhydride or an active ester, in an inert solvent in the presence of bases. As inert solvents, there come into question, for example, methylene chloride, benzene, dimethylformamide or the like.

Since the subsequent splitting off of the protective group $R_3$ and/or $R_4$ by hydrolysis could also lead to the hydrolysis of the just introduced acyl function $R_2$, before the acylation those protective groups $R_3$ and/or $R_4$ are to be introduced which can be removed again in other ways, e.g. by hydrogenation.

For the case that $R_4$ signifies a group —CH($R_5$-)COOH, compounds of the general formula I can be prepared especially well in that, instead of reaction components with free carboxyl group, those with "masked carboxyl function" are employed. One then first obtains compounds of the general formula I in which $R_4$ represents a group —CH($R_5$)—Y, whereby Y can have the meaning alkoxycarbonyl, aminocarbonyl, cyano, formyl, hydroxymethyl, aminomethyl or an ortho ester group. The conversion of these groups into the carboxyl function then takes place according to processes known from the literature by hydrolysis (alkoxycarbonyl, cyano, ortho,ester) or oxidation (formyl, hydroxymethyl, aminomethyl).

On the other hand, however, one can also esterify the carboxylic acids I, $R_4$=—CH($R_5$)—COOH, in the usual way, whereby compounds I, $R_4$=—CH($R_5$)—COOR$_6$ result (for the extent of the meaning of $R_6$, see further below) or convert their esters with a particular radical R by transesterification into an ester with another radical R. The esterification of the carboxylic acids is expediently carried out in the presence of an acidic catalyst, such as e.g. hydrogen chloride, sulphuric acid, p-toluenesulphonic acid, or of a strongly acidic ion exchange resin. On the other hand, transesterifications require the addition of a small amount of a basic substance, e.g. of an alkali metal or alkaline earth metal hydroxide or of an alkali metal alcoholate. For the esterification of the carboxyl group or for a transesterification, in principle all alcohols are suitable. Preferred are the lower monohydroxy alcohols, such as methanol, ethanol or propanol, as well as polyhydroxy alcohols, e.g. glycerol, or alcohols with other functional groups, such as ethanolamine or glycerol ethers.

The amides according to the invention derived from the carboxylic acids of the general formula I, $R_4$=—CH($R_5$)—COOH, are preferably prepared by per se known methods from the carboxylic acids or their reactive derivatives (such as e.g. carboxylic acid halides, esters, azides, anhydrides or mixed anhydrides) by reaction with amines. As amino components, there come into question e.g. ammonia, alkylamines, dialkylamines but also aminoalcohols, such as e.g. ethanolamine and 2-aminopropanol. Other valuable amine components are alkyl-, aralkyl- and arylpiperazines.

For the preparation of salts with pharmacologically compatible organic or inorganic bases, such as e.g. sodium hydroxide, potassium hydroxide, calcium hydroxide, ammonium hydroxide, methylglucamine, morpholine or ethanolamine, the carboxylic acids can be reacted with the appropriate bases. Mixtures of the carboxylic acids with a suitable alkali metal carbonate or hydrogen carbonate also come into consideration.

One obtains pure enantiomers of the compounds of the formula I either by racemate resolution (vis salt formation with optically-active bases) or in that in each case one uses optically pure amines/ amino acids in the syntheses according to processes c) and d)–f).

For the preparation of medicaments, the compounds of the general formula I are mixed in per se known manner with suitable pharmaceutical carrier substances, aroma, flavouring and colouring materials and formed, for example, into tablets or costed tablets or, with addition of appropriate adjuvants, suspended or dissolved in water or oil, such as e.g. olive oil.

The substances of the general formula I can be administered orally and parenterally in liquid or solid form. As injection medium, it is preferred to use water which contains the stabilising agents, solubilising agents and/or buffers usual in the case of injection solutions. Such additives are e.g. tartrate or borate buffers, ethanol, dimethyl sulphoxide, complex formers (such as ethylenediaminetetraacetic acid), high molecular polymers (such as liquid polyethylene oxide) for viscosity regulation or polyethylene derivatives of sorbitol anhydrides.

Solid carrier materials are e.g. starch, lactose, mannitol, methyl cellulose, talc, highly dispersed silicic acid, high molecular ferry acids (such as stearic acid), gelatine, agar-agar, calcium phosphate, magnesium stearate, animal and vegetable fats or solid high molecular polymers (such as polyethylene glycols). Compositions suitable for oral administration can, if desired, contain flavouring and sweetening materials.

Preferred in the meaning of the invention are, apart from the compounds of the formula I mentioned in the Examples, the following:

1) 1-[2-[2-(4-chlorophenylsulphonylamino)-ethyl]-phenoxy]-2-aminoethane
2) 1-[3-[2-(4-chlorophenylsulphonylamino)-ethyl]-phenoxy]-3-aminopropane
3) 1-[3-[2-(4-chlorophenylsulphonylamino)-ethyl]-phenoxy]-4-aminobutane; hydrochloride, m.p. 153° C.
4) 1-[3-[2-(4-methylphenylsulphonylamino)-ethyl]-phenoxy]-2-aminoethane; hydrochloride, m.p. 128°–130° C.
5) 1-[3-[2-(trifluoromethylphenylsulphonylamino)-ethyl]-phenoxy]-2-aminoethane
6) 1-[4-[2-(4-chlorophenylsulphonylamino)-ethyl]-phenoxy]-4-aminobutane
7) 1-[4-[2-(4-methylphenylsulphonylamino)-ethyl]-phenoxy]-2-piperidinoethane
8) 1-[3-[2-(4-methylphenylsulphonylamino)-ethyl]-phenoxy]-2-piperidinoethane
9) 1-[3-[2-(4-chlorophenylsulphonylamino)-ethyl]-phenoxy]-2-anilinoethane; hydrochloride, m.p. 124°–126° C.
10) 1-[3-[2-(4-chlorophenylsulphonylamino)-ethyl]-phenoxy]-2-cyclohexylaminoethane; hydrochloride, m,p, 150°–151° C.
11) N-[2-[3-[2-(4-chlorophenylsulphonylamino)-ethyl]-phenoxy]-ethyl]-glycine
12) N-[2-[3-[2-(4-chlorophenylsulphonylamino)-ethyl]-phenoxy]-ethyl]-L-alanine
13) N-[2-[4-[2-(4-chlorophenylsulphonylamino)-ethyl]-phenoxy]ethyl]-L-alanine
14) N-[2-[3-[2-(4-methylphenylsulphonylamino)-ethyl]-phenoxy]-ethyl]-L-alanine
15) N-[2-[3-[2-(4-chlorophenylsulphonylamino)-ethyl]-phenoxy]-ethyl]-phenylalanine
16) N-[4-[2-(4-chlorophenylsulphonylamino)-ethyl]-benzyl]-glycine
17) N-[4-[2-(4-chlorophenylsulphonylamino)-ethyl]-benzyl]-L-alanine
18) N-[4-[2-(4-chlorophenylsulphonylamino)-ethyl]-phenethyl]-glycine
19) N-[4-[2-(4-chlorophenylsulphonylamino)-ethyl]-phenethyl]-L-alanine
20) 1-[4-[2-(4-chlorophenylsulphonylamino)-ethyl]-phenoxy]-2-(3-pyridylamino)-ethane
21) 1-[4-[2-(4-chlorophenylsulphonylamino)-ethyl]-phenyl]-2-(4-pyridylamino)-ethane
22) 1-[4-[2-(4-chlorophenylsulphonylamino)-ethyl]-phenyl]-2-(2-pyridylamino)-ethane
23) 1-[4-[2-(4-chlorophenylsulphonylamino)-ethyl]-2-(3-pyrazolylamino)-ethane
24) N-[2-[4-[2-(4-chlorophenylsulphonylamino)-ethyl]-phenyl]-ethyl]-pyrrole
25) N-[2-[4-[2-(4-chlorophenylsulphonyl)-ethyl]-phenoxy]-ethyl]-pyrrole
26) N-[2-[4-[2-(4-chlorophenylsulphonylamino)-ethyl]-phenyl]-ethyl]-imidazole
27) N-[2-[4-[2-(4-chlorophenylsulphonylamino)-ethyl]-phenoxy]-ethyl]-imidazole
28) N-[2-[4-[2-(4-chlorophenylsulphonylamino)-ethyl]-phenyl]-ethyl]-pyrazole
29) N-[2-[4-[2-(4-chlorophenylsulphonylamino)-ethyl]-phenoxy]-ethyl]-pyrazole
30) N-[2-[4-[2-(4-chlorophenylsulphonylamino)-ethyl]-phenyl]-ethyl]-indole
31) N-[2-[4-[2-(4-chlorophenylsulphonylamino)-ethyl]-phenoxy]-indole
32) N-[2-[4-[2-(4-chlorophenylsulphonylamino)-ethyl]-phenyl]-ethyl]-carbazole
33) 1-[4-[2-(4-chlorophenylsulphonylamino)-ethyl]-phenoxy]-2-(2-pyridinylamino)-ethane
34) 1-[4-[2-(4-chlorophenylsulphonylamino)-ethyl]-phenoxy]-2-(3-pyridinylamino)-ethane
35) 1-[4-[2-(4-chlorophenylsulphonylamino)-ethyl]-phenoxy]-2-(4-pyridinylamino)-ethane
36) 1-[3-[2-(4-chlorophenylsulphonylamino)-ethyl]-phenoxy]-2-(2-pyridinylamino)-ethane
37) 1-[3-[2-(4-chlorophenylsulphonylamino)-ethyl]-phenoxy]-2-(3-pyridinylamino)-ethane
38) 1-[3-[2-(4-chlorophenylsulphonylamino)-ethyl]-phenoxy]-2-(4-pyridinylamino)-ethane
39) 1-[4-[2-(4-chlorophenylsulphonylamino)-ethyl]-phenyl]-2-(2-pyridinylamino)-ethane
40) 1-[4-[2-(4-chlorophenylsulphonylamino)-ethyl]-phenyl]-2-(3-pyridinylamino)-ethane
41) 1-[4-[2-(4-chlorophenylsulphonylamino)-ethyl]-phenyl]-2-(4-pyridinylamino)-ethane.

Also preferred are new carbonamides of the formula II as intermediate products which lead to the preferred compounds nos. 1–10 and 20–41, as well as the compounds described in Examples 1–3.

The following Examples show some of the numerous process variants which can be used for the synthesis of the compounds according to the invention. However they are not to represent a limitation in the meaning of the inventive concept.

PRECURSORS: CARBOXYLIC ACID AMIDES OF THE GEN. FORMULA II

Example 1

2-[4-[2-(4-Chlorophenylsulphonylamino)-ethyl]-phenyl]-acetic acid piperidide

A mixture of 10.0 g (28 mmol) 2-[4-[2-(4-chlorophenylsulphonylamino)-ethyl]-phenyl]-acetic acid, 10 ml thionyl chloride and 3 drops of DMF is stirred for 2 hrs. at 60° C. One then distils off excess thionyl chloride in a vacuum and dissolves the residue in 50 ml methylene chloride. One adds this solution dropwise, with ice cooling, to a solution of 7.22 g (85 mmol) piperidine in 80 ml methylene chloride. Subsequently, it is stirred for 1 hr. with ice cooling, then for 1 hr. at room temperature. One then shakes successively twice with 2N HCl, twice with water and twice with NaHCO$_3$ solution. One then dries over magnesium sulphate, evaporates and recrystallises from ethyl acetate. Yield: 7.2 g (61%); m.p. 110° C.

In analogy thereto was prepared:

a) 3-[4-[2-(4-chlorophenylsulphonylamino)-ethyl]-phenyl]-propionamide from 3-[4-[2-(4-chlorophenylsulphonylamino)-ethyl]-phenyl]-propionic acid, SOCl$_2$ and ammonia. The acid chloride was dissolved in methylene chloride, then gassed with ammonia.

Yield 77% of theory; m.p. 169°–170° C. (methanol).

b) 4-[2-(4-chlorophenylsulphonylamino)-ethyl]-phenylacetamide from 4-[2-(4-chlorophenylsulphonylamino)-ethyl]-phenylacetic acid, SOCl$_2$ and ammonia.

Yield 76% of theory; m.p. 192°–193° C.

c) 4-[2-(4-chlorophenylsulphonylamino)-ethyl]-phenylacetic acid ethylamide from 4-[2-(4-chlorophenylsulphonylamino-ethyl]-phenylacetic acid, SOCl$_2$ and ethylamine.

Yield 62% of theory; m.p. 113° C. (aq. ethanol).

Furthermore, from 3-[2-(4-chlorophenylsulphonylamino)-ethyl]-phenoxyacetic acid, SOCl$_2$ and the corresponding amine were also prepared:

d) 3-[2-(4-chlorophenylsulphonylamino)-ethyl]-phenoxyacetylpiperidide yield 77% of theory, m.p. 124°–126° C. (ethanol)

e) 3-[2-(4-chlorophenylsulphonylamino)-ethyl]-phenoxyacetyldiethylamide yield 87% of theory; m.p. 78°–80° C. (ethyl acetate+isohexane)

f) 3-[2-(4-chlorophenylsulphonylamino)-ethyl]-phenoxyacetic acid (2-hydroxyethylamide)

yield 65% of theory; colourless oil g) 3-[2-(4-chlorophenylsulphonylamino)-ethyl]-phenoxyacetic acid 2-[bis-(2-hydroxyethyl)-amide]

yield 66% of theory; colourless oil h) 3-[2-(4-chlorophenylsulphonylamino)-ethyl]-phenoxyacetic acid morpholide yield 86% of theory; m.p. 110°–111° C. (ethanol)

i) 3-[2-(4-chlorophenylsulphonylamino)-ethyl]-phenoxyacetic acid (4-methylpiperazide)

yield 98% of theory; m.p. 139°–141° C. (ethanol)

j) 3-[2-(4-chlorophenylsulphonylamino)-ethyl]-phenoxyacetic acid anilide yield 89% of theory; m.p. 143°–144° C.

k) 3-[2-(4-chlorophenylsulphonylamino)-ethyl]-phenoxyacetic acid cyclohexylamide yield 82% of theory; m.p. 100°–101° C.

In the case of the use of 3-[2-(3-trifluoromethylphenylsulphonylamino)-ethyl]-phenoxyacetic acid or of 3-[2-(4-bromophenylsulphonylamino)-ethyl]-phenoxyacetic acid, one obtains with SOCl$_2$ and ammonia the compounds:

l) 3-[2-(3-trifluoromethylphenylsulphonylamino)-ethyl]-phenoxyacetamide yield 71% of theory; m.p. 118° C. (ethanol)

m) 3-[2-(4-bromophenylsulphonylamino)-ethyl]-phenoxyacetamide yield 81% of theory; m.p. 115°–116° C. (ethanol)

From 4-[2-(4-chlorophenylsulphonylamino)-ethyl]-phenoxyacetic acid, SOCl$_2$ and the corresponding amine, one obtains:

n) 4-[2-(4-chlorophenylsulphonylamino)-ethyl]-phenoxyacetic acid diethylamide yield 80% of theory; colourless oil.

o) 4-[2-(4-chlorophenylsulphonylamino)-ethyl]-phenoxyacetic acid ethylamide yield 81% of theory; m.p. 133°–134° C.

p) 4-[2-(4-chlorophenylsulphonylamino)-ethyl]-phenoxyacetic acid (4-methylpiperazide)

yield 78% of theory; m.p. 110°–112° C.

q) 4-[2-(4-chlorophenylsulphonylamino)-ethyl]-phenoxyacetic acid (2-pyrimidinyl)-amide yield 60% of theory; hydrochloride m.p. 150°–157° C.

r) 4-[2-(4-chlorophenylsulphonylamino)-ethyl]-phenoxyacetic acid (3-pyridyl)-amide yield 50% of theory; hydrochloride m.p. 152°–155° C., Example 2

4-[3-[2-(4-Chlorophenylsulphonylamino)-ethyl]-phenoxy]-butyramide

To a solution cooled to −10° C. of 100 ml abs. THF, 4.32 g (43 mmol) triethylamine and 14.4 g (36 mmol) 4-[3-[2-(4-chlorophenylsulphonylamino)-ethyl]-phenoxy]butyric acid one slowly adds dropwise a mixture of 4.02 g (37 mmol) chloroformic acid ethyl ester and 30 ml abs. THF. One allows to come to room temperature, stirs a further 30 min and filters off with suction the precipitated triethylamine hydrochloride. The filtrate is then gassed with ammonia with ice cooling. It is then stirred for 6 hrs. at room temperature, evaporated and mixed with 2N HCl. One adds ethyl acetate thereto, mixes up very vigorously and separates the phases. The ethyl acetate phase is shaken out twice with bicarbonate solution and twice with water, then dried with Na$_2$SO$_4$ and evaporated. After recrystallisation from ethyl acetate, one obtains colourless crystals. Yield: 12.8 g (89% of theory); m.p. 110°–112° C.

In an analogous way, there can be prepared:

a) 3-[2-(4-chlorophenylsulphonylamino)-ethyl]-phenoxyacetic acid ethylamide

Yield 83% of theory; colourless oil.

b) 4-[2-(4-chlorophenylsulphonylamino)-ethyl]-phenylacetic acid (4-pyridyl)-amide Yield 21% of theory; hydrochloride m.p. 181° C.

A variant of the process consists in the use of an active nitrophenyl ester for the amide formation:

c) 3-[2-(4-methylphenylsulphonylamino)-ethyl]-phenoxyacetic acid piperidide.

To a 40° C. warm solution of 12.0 g (34 mmol) 3-[2-(4-methylphenylsulphonylamino)-ethyl]-phenoxyacetic acid and 120 ml abs. THF one adds 5.6 g (34 mmol) carbonylbisimidazole, allows to react for 15 min. and then adds 0.5 g (3.4 mmol) 4-nitrophenol thereto, again allows to react for 15 min. and now adds 2.92 g (34 mmol) piperidine thereto. It is now maintained at 60° C. for two hours. One then evaporates, mixes the residue with en iced water-hydrochloric acid mixture until the reaction was distinctly acidic and extracts three times with ethyl acetate. The extract is washed three times with water, twice with 2N Na$_2$CO$_3$ solution and once with water, one then dries (Na$_2$SO$_4$) and evaporates. Yield 10.4 g (73% of theory); m.p. 119°–120° C. (ethanol).

In a manner analogous to c), from 4-[2-(4-chlorophenylsulphonylamino)-ethylbenzoic acid and piperidine was prepared:

d) 4-[2-(4-chlorophenylsulphonylamino)-ethyl]-benzoic acid piperidide

Yield 62% of theory; m.p. 190° C.

and from 3-[4-[2-(4-chlorophenylsulphonylamino)-ethyl]-phenyl]-propionic acid and piperidine is prepared:

e) 3-[4-[2-(4-chlorophenylsulphonylamino)-ethyl]-phenyl]-propionic acid piperidide Yield 71% of theory; m.p. 89°–91° C.

Example 3

4-[2-(4-Chlorophenylsulphonylamino)-ethyl]-phenoxyacetic acid [bis-(2-hydroxyethyl)-amide]

One maintains a mixture of 9.44 g (25 mmol) 4-[2-(4-chlorophenylsulphonylamino)-ethyl]-phenoxyacetic acid ethyl ester, 30 ml methanol and 30 ml diethanolamine at reflux temperature for five hrs. and subsequently evaporates. The residue is mixed with 300 ml acetic acid ethyl ester. One stirs this solution with so much 2N HCl that the aqueous phase reacts acid. It is separated off, the ethyl acetate phase is washed neutral with water, dried ($Na_2SO_4$) and subsequently evaporated. Yield 9.1 g (80% of theory); colourless oil.

In an analogous way, from 4-[2-(4-chlorophenylsulphonylamino)-ethyl]-phenoxyacetic acid ethyl ester and the appropriate amine were prepared:

a) 4-[2-(4-chlorophenylsulphonylamino)-ethyl]-phenoxyacetic acid (2-hydroxyethylamide)
Yield 91% of theory; m.p. 112°–114° C.

b) 4-[2-(4-chlorophenylsulphonylamino)-ethyl]-phenoxyacetic acid piperidide
Yield 93% of theory; m.p. 124°–126° C.

c) 4-[2-(4-chlorophenylsulphonylamino)-ethyl]-phenoxyacetic acid morpholide
Yield 91% of theory; colourless oil d) 4-[2-(4-chlorophenylsulphonylamino)-ethyl]-phenoxyacetamide
The ester is dissolved in methanol. One adds liquid $NH_3$ thereto in the cold, allows excess $NH_3$ to evaporate off at room temperature and filters off the precipitated product with suction. Yield 88% of of theory; m.p. 158°–159° C.

AMINES OF GEN. FORMULA I

Example 4

1-[3-[2-(4-Chlorophenylsulphonylamino)-ethyl]-phenoxy]-2-aminoethane

To a suspension of 1.55 g (41 mmol) $LiAlH_4$ and 200 ml abs. THF one adds dropwise at room temperature, while stirring, a solution of 10.0 g (27 mmol) 3-[2-(4-chlorophenylsulphonylamino)-ethyl]-phenoxyacetamide (prep. described in EP 89115 911.3, Example 14) and 150 ml abs. THF. The mixture is maintained for two hrs. at reflux temperature, then cooled and decomposed with ice water. One filters off with suction and evaporates the filtrate. The oil remaining behind is taken up in methylene chloride. One dries ($MgSO_4$), dissolves in ether and precipitates the hydrochloride by addition of hydrogen chloride-containing ether. After recrystallisation from ethanol, one obtains colourless crystals. Yield; 9.3 g (88% of theory); m.p. of the hydrochloride: 183° C.

In analogous manner are prepared:

a) 1-[3-[2-(4-chlorophenylsulphonylamino)-ethyl]-phenoxy]-2-diethylaminoethane
from 3-[4-[2-(4-chlorophenylsulphonylamino]-ethyl]-phenoxyacetic acid diethylamide
Yield 77% of theory; colourless oil, $n_D^{20}=1.5552$ b) 1-[3-[2-(4-chlorophenylsulphonylamino)-ethyl]-phenoxy]-2-(1-piperidyl)-ethane
from 3-[2-(4-chlorophenylsulphonylamino)-ethyl]-phenoxyacetic acid piperidide
Yield 90% of theory; colourless oil, $n_D^{20}=1.5656$ c) 1-[3-[2-(4-chlorophenylsulphonylamino)-ethyl]-phenoxy]-2-(1-morpholinyl)-ethane
from 3-[2-(4-chlorophenylsulphonylamino)-ethyl]-phenoxyacetic acid morpholide
Yield 85% of theory; colourless oil, $n_D^{20}=1.5633$ d) 1-[3-[2-(4-chlorophenylsulphonylamino)-ethyl]-phenoxy]-2-(4-methyl-1-piperazinyl)-ethane
from 3-[2-(4-chlorophenylsulphonylamino)-ethyl]-phenoxyacetic acid (4-methylpiperazide)
Yield 86% of theory; m.p. of the dimaleinate: 161°–163° C. The free base is a colourless oil; $n_D^{20}=1.5578$ e) 1-[3-[2-(4-chlorophenylsulphonylamino)-ethyl]-phenoxy]-2-(2-hydroxyethylamino)-ethane
from 3-[2-(4-chlorophenylsulphonylamino)-ethyl]-phenoxyacetic acid (2-hydroxyethylamide)
Yield 73% of theory; base: colourless oil, $n_D^{20}=$ f) 1-[3-[2-(4-chlorophenylsulphonylamino)-ethyl]-phenoxy]-2-[bis-(2-hydroxyethyl)-amino]-ethane
from 3-[2-(4-chlorophenylsulphonylamino)-ethyl]-phenoxyacetic acid [bis-(2-hydroxyethyl)-amide]
Yield 60% of theory; colourless oil g) 1-[4-[2-(4-chlorophenylsulphonylamino)-ethyl]-phenoxy]-2-aminoethane
from 4-[2-(4-chlorophenylsulphonylamino)-ethyl]-phenoxyacetamide
Yield 60% of theory; m.p. of hydrochloride 251°–253° C.

h) 1-[4-[2-(4-chlorophenylsulphonylamino)-ethyl]-phenoxy]-2-diethylaminoethane
from 4-[2-(4-chlorophenylsulphonylamino)-ethyl]-phenoxyacetic acid diethylamide
Yield 58% of theory; colourless oil i) 1-[4-[2-(4-chlorophenylsulphonylamino)-ethyl]-phenoxy]-2-(1-piperidyl)-ethane from 4-[2-(4-chlorophenylsulphonylamino)-ethyl]-phenoxyacetic acid piperidide
Yield 57% of theory; m.p. of hydrochloride 78°–81° C.

j) 1-[4-[2-(4-chlorophenylsulphonylamino)-ethyl]-phenoxy]-2-(1-morpholinyl)-ethane
from 4-[2-(4-chlorophenylsulphonylamino)-ethyl]-phenoxyacetic acid morpholide
Yield 53% of theory; m.p. of hydrochloride 177°–179° C.

k) 1-[4-[2-(4-chlorophenylsulphonylamino)-ethyl]-phenoxy]2-(2-hydroxyethylamino)-ethane
from 4-[2-(4-chlorophenylsulphonylamino)-ethyl]-phenoxyacetic acid (2-hydroxyethylamide)
Yield 62% of theory; m.p. of hydrochloride: 206°–208° C.

l) 1-[4-[2-(4-chlorophenylsulphonylamino)-ethyl]-phenoxy]2-[bis-(2-hydroxyethyl)-amino]-ethane
from 4-[2-(4-chlorophenylsulphonylamino)-ethyl]-phenoxyacetic acid [bis-(2-hydroxyethyl)-amide
Yield 44% of theory; hydrochloride: glassy mass m) 1-[4-[2-(4-chlorophenylsulphonylamino)-ethyl]-phenyl]-3-aminopropane
from 3-[4-[2-(4-chlorophenylsulphonylamino)-ethyl]-phenyl]-propionamide
Yield 74% of theory; m.p. 124° C. (ethyl acetate)

n) 1-[4-[2-(4-chlorophenylsulphonylamino)-ethyl]-phenyl]-2-(1-piperidyl)-ethane
from 2-[4-[2-(4-chlorophenylsulphonylamino)-ethyl]-phenyl]-acetic acid piperidide
Yield 51% of theory; m.p. 76°–78° C.

o) 1-[4-[2-(phenylsulphonylamino)-ethyl]-phenoxy]-2-aminoethane
from 4-[2-(phenylsulphonylamino)-ethyl]-phenoxyacetamide Yield 56% of theory; m.p. of hydrochloride 197°–199° C.

p) 1-[4-[2-(phenylsulphonylamino)-ethyl]-phenoxy]-2-(4-methylpiperazinyl)-ethane
from 4-[2-(phenylsulphonylamino)-ethyl]-phenoxyacetic acid (4-methylpiperazide)
Yield 35% of theory; dihydrochloride m.p. 104°–114° C.

q) 1-[4-[2-(4-chlorophenylsulphonylamino)-ethyl]-phenoxy]-2-(4-methylpiperazinyl)-ethane
from 4-[2-(4-chlorophenylsulphonylamino)-ethyl]-phenoxyacetic acid (4-methylpiperazide)
Yield 41% of theory; dihydrochloride m.p. 187°–193° C.

r) 1-[4-[2-(4-chlorophenylsulphonylamino)-ethyl]-phenyl]-3-(1-piperidyl)-propane
from 3-[4-[2-(4-chlorophenylsulphonylamino)-ethyl]-phenyl]-propionic acid piperidide
Yield 64% of theory; m.p. 87°–88° C.

s) 1-[4-[2-(4-chlorophenylsulphonylamino)-ethyl]-phenyl]-4-aminobutane
from 4-[4-[2-(4-chlorophenylsulphonylamino)-ethyl]-phenyl]-butyramide
Yield 71% of theory; hydrogen sulphate m.p. 230°–233° C.

t) 1-[3-[2-(4-chlorophenylsulphonylamino)-ethyl]-phenoxy]-aminobutane
from 4-[3-[2-(4-chlorophenylsulphonylamino)-ethyl]-phenoxy]-butyramide
Yield 66% of theory; hydrochloride m.p. 153° C.

u) 1-[3-[2-(4-chlorophenylsulphonylamino)-ethyl]-phenoxy]-2-(ethylamino)-ethane
from 3-[2-(4-chlorophenylsulphonylamino)-ethyl]-phenoxyacetic acid ethylamide
Yield 48% of theory; hydrochloride m.p. 163°–165° C.

v) 1-[3-[2-(4-methylphenylsulphonylamino)-ethyl]-phenoxy]-2-(cyclohexylamino)-ethane
from 3-[2-(4-methylphenylsulphonylamino)-ethyl]-phenoxyacetic acid cyclohexylamide
Yield 85% of theory; hydrochloride as viscous oil w) 1-[4-[2-(4-chlorophenylsulphonylamino)-ethyl]-phenoxy]-2-(ethylamino)-ethane
from 4-[2-(4-chlorophenylsulphonylamino)-ethyl]-phenoxyacetic acid ethylamide
Yield 40% of theory; hydrochloride m.p. 234°–236° C.

x) N-(4-[2-(4-chlorophenylsulphonylamino)-ethyl]-benzyl)-piperidine
from 4-[2-(4-chlorophenylsulphonylamino)-ethyl]-benzoic acid piperidide
Yield 66% of theory; hydrochloride m.p. 197°–199° C.

Example 5

1-[4-[2-(4-Chlorophenylsulphonylamino)-ethyl]-phenyl]-2-aminoethane

To a 0° C. cold abs. ether (250 ml) one adds in small portions 1.63 g (12 mmol) AlCl$_3$, thereafter 0.47 g (12 mmol) LiAlH$_4$. To the suspension one now adds dropwise a solution of 4.1 g (12 mmol) 4-[2-(4-chlorophenylsulphonylamino)-ethyl]-benzyl cyanide and 75 ml ether. One now maintains at reflux temperature for two hrs., cools and decomposes with an ice/ NaHCO$_3$ solution. One filters and extracts the Al(OH)$_3$ slurry several times with hot ethyl acetate. The ethyl acetate solution is dried (MgSO$_4$) and evaporated. After recrystallisation from ethyl acetate, the yield amounts to 2.3 g (55% of theory); m.p. 113°–114° C.

In an analogous way is prepared:
a) 1-[3-[2-(4-chlorophenylsulphonylamino)-ethyl]-phenoxy]-2-cyanoethane, m.p. 90°–93° C. which can be prepared by heating to 110° C. for 5 hours s mixture of 3-[2-[4-chlorophenylsulphonylamino)-ethyl]-phenoxy]-acetamide (1 mol), P$_2$O$_5$ (2 mol) and toluene. Yield 63% of theory; m.p. 94° C.

Example 6

1-[3-[2-(4-Chlorophenylsulphonylamino)-ethyl]-phenoxy]-2-acetaminoethane

One stirs a suspension of 2.0 g (5.1 mmol) 1-[3-[2-(4-chlorophenylsulphonylamino)-ethyl]-phenoxy]-2-aminoethane hydrochloride (see Example 1), 50 ml methylene chloride and 1.56 g (15.3 mmol) abs. triethylamine for 15 min, adds thereto a catalytic amount of 4-dimethylaminopyridine and cools to 0° C. A solution of 0.4 g (5.1 mmol) acetyl chloride and 4 ml abs. methylene chloride is now added thereto dropwise. After two hours, one extracts twice with dil. HCl and then with water, dries with MgSO$_4$ and evaporates. The oil remaining behind is chromatographed on silica gel with the elution agent methylene chloride. After evaporation, one obtains a colourless oil, yield 1.3 g (64% of theory).

In an analogous manner, one obtains with benzoyl chloride
a) 1-[3-[2-(4-chlorophenylsulphonylamino)-ethyl]-phenoxy]-2-benzoylaminoethane
Yield 76% of theory; colourless oil.

Example 7

1-[3-[2-(4-Chlorophenylsulphonylamino)-ethyl]-phenoxy]-2-(cyclohexylamino)-ethane At ice-bath temperature, one mixes 5.5 g (12.2 mmol) 5-[2-(4-chlorophenylsulphonylamino)-ethyl]-phenoxyacetic acid cyclhexylamide with 13 ml (0.142 mol) POCl$_3$, then removes the icebath and stirs for 20 minutes at room temperature. Excess POCl$_3$ is then distilled off in a vacuum at 20° C. and the residue is dissolved in 40 ml ethylene glycol dimethyl ether. One again cools to icebath temperature and adds thereto 1.52 g (40 mmol) NaBH$_4$ portionwise with vigorous stirring. Subsequently, it is stirred for 16 hours at room temperature. After again cooling to 0° C., one mixes with 25 ml methanol which contains 1 mol HCl per liter and stirs for a further hour in an icebath. Subsequently, it is evaporated at 30° C., one adds 50 ml 2N Na$_2$CO$_3$ solution thereto, extracts with ethyl acetate, dries the extract with Na$_2$SO$_4$ and evaporates. After addition of ether and some acetone, it is filtered off with suction and recrystallised from ethanol. Yield 4.7 g (82% of theory); hydrochloride m.p. 150°–151° C.

In an analogous way, from the appropriate carbonamides are prepared:
a) 1-[3-[2-(4-chlorophenylsulphonylamino)-ethyl]-phenoxy]-3-anilinoethane
Yield 66% of theory of hydrochloride with the m.p. 124°–126° C.

b) 1-[4-[2-(4-chlorophenylsulphonylamino)-ethyl]-phenyl]-2-ethylaminoethane
Yield 62% of theory; m.p. 212° C.

c) 1-[3-[2-(3-trifluoromethylphenylsulphonylamino)-ethyl]-phenoxy]-2-aminoethane Yield 5% of theory of hydrochloride with the m.p. 159°–161° C.

d) 1-[3-[2-(4-bromophenylsulphonylamino)-ethyl]-phenoxy]-2-aminoethane

Yield 48% of theory of hydrochloride with the m.p. 183°–185° C.

e) 1-[4-[2-(4-trifluoromethylphenylsulphonylamino)-ethyl]-phenoxy]-2-(N-alaninyl)-ethane from 4-[2-(4-trifluoromethylphenylsulphonylamino)-ethyl]-phenoxyacetic acid (alanine ethyl ester)-amide (m.p. 109°–114° C.) and subsequent hydrolysis of the ethyl ester Yield 31% of theory; hydrochloride m.p. 187°–191° C.

f) 1-[4-[2-(4-chlorophenylsulphonylamino)-ethyl]-phenoxy]-2-(N-alaninyl)-ethane from 4-[2-(4-chlorophenylsulphonylamino)-ethyl]-phenoxyacetic acid (alanine ethyl ester)-amide and subsequent hydrolysis of the ethyl ester Yield 43% of theory; hydrochloride m.p. 117°–153° C. (decomp.)

g) 1-[3-[2-(4-chlorophenylsulphonylamino)-ethyl]-phenoxy]-2-(L-N-alaninyl)-ethane from 3-[2-(4-chlorophenylsulphonylamino)-ethyl]-phenoxy]-acetic acid (L-alanine ethyl ester)-amide and subsequent hydrolysis of the ethyl ester Yield 54% of theory; m.p. 70° C.

h) 1-[4-[2-(4-chlorophenylsulphonylamino)-ethyl]-phenyl]-2-(L-2-hydroxy-1-methyl)-ethane Yield 39% of theory; hydrochloride m.p. 181°–184° C. (ethanol)

i) 1-[3-[2-(4-methylphenylsulphonylamino)-ethyl]-phenoxy]-2-(L-2-hydroxy-1-methyl)-ethane Yield 61% of theory; hydrochloride: highly viscous oil j) 1-[3-[2-(4-chlorophenylsulphonylamino)-ethyl]-phenoxy]-2-(L-2-hydroxy-1-phenylmethyl)-ethane Yield 67% of theory; hydrochloride: highly viscous oil

Example 8

1-[3-[2-(4-Chlorophenylsulphonylamino)-ethyl]-phenoxy]-2-aminoethane

To a solution of 21.6 g (58.6 mmol) 3-[2-(4-chlorophenylsulphonylamino)-ethyl]-phenoxyacetamide and 175 ml dimethoxyethane one adds portionwise at 15°–20° C. 31.3 g (0.234 mol) anhydrous aluminium chloride and allows to stir further for 30 min. One then adds 8.85 g (0.234 mol) NaBH4 portionwise thereto at 15°–20° C. within ½ hr. After 3 hrs. stirring while cooling, 130 ml ice-water are carefully added dropwise thereto, whereby the internal temperature is not to exceed 25° C. While cooling with ice, one brings the pH value to 8.5 by addition of conc. NaOH, adds 75 ml ethyl acetate thereto and filters. The precipitate is after-washed with ethyl acetate. After separation of the phases, the aqueous phase is also extracted with ethyl acetate. The organic extracts are dried, concentrated to about 80 ml and mixed with 20 ml HCl-containing ether. After cooling, one filters off with suction and then washes with ethyl acetate. Yield 16.7 g (73% of theory) of hydrochloride with the m.p. 187°–190° C.

Example 9

1-[3-[2-(4-Chlorophenylsulphonylamino)-ethyl]-phenoxy]-3-aminopropane

1.

1-[3-[2-(Benzyloxycarbonylamino)-ethyl]-phenoxy]-3-(N-phthalimido)-propane

A mixture of 24.4 g (90 mmol) 3-[2-(benzyloxycarbonylamino)-ethyl]-phenol, 31.3 g (117 mmol) 1-bromo-3-(N-phthalimido)-propane, 16.1 g (117 mmol) powdered dry potassium carbonate and 100 ml abs. DMF is stirred for 20 hrs. at 80° C. One then cools, mixes with ice water and extracts several times with ethyl acetate. After drying (Na2SO4), the organic phase is evaporated and the oily residue stirred with a methanol-water mixture (70:30 vol.), whereby it crystallises. After filtering off with suction, washing with water, dissolving in ethyl acetate and drying (Na2SO4), it is again evaporated, then stirred with isohexane, filtered off with suction and dried. Yield 36.4 g (88% of theory); m.p. 84°–85° C.

2.

1-[3-(2-Aminoethyl)-phenoxy]-3-(N-phthalimido)-propane

One hydrogenates a mixture of 15.0 g (32.5 mmol) of the compound obtained according to 1., 1 l of methanol and 6.5 g of palladium-charcoal (10 percent) for 24 hrs. at room temperature and normal pressure and subsequently suction-filters from the catalyst. The filtrate is mixed with HCl-containing ether and evaporated. After stirring with isohexane, filtering off with suction and drying, yield 9.15 g (78% of theory) of hydrochloride; m.p. 132°–136° C. (ethanol).

3.

1-[3-[2-(4-Chlorophenylsulphonylamino)-ethyl]-phenoxy]-3-(N-phthalimidio)-propane To a suspension of 6.10 g (16.6 mmol) 1-[3-(2-aminoethyl)-phenoxy]-3-(N-phthalimido)-propane hydrochloride, 70 ml methylene chloride and 5.06 g triethylamine, after 15 min. stirring and after cooling to 0° C., one slowly adds dropwise thereto a mixture of 3.6 g (17.1 mmol) 4-chlorobenzenesulphochloride and 40 ml methylene chloride. It is then after-stirred for one hr. at 0° C. and one hr. at room temperature. One dilutes with 100 ml methylene chloride and extracts twice with dil. HCl, then twice with water, dries (MgSO4) and evaporates. The residue is recrystallised from ethanol. Yield 6.79 g (82% of theory); m.p. 118° C.

Title Compound

A mixture of 3.6 g (7.2 mmol) of the phthalimido compound obtained according to 3., 40 ml ethanol and 5 ml 100 percent hydrazine hydrate (=100 mmol) is stirred for 5 hrs at 50° C., then brought to pH 6.8 with very dil. hydrochloric acid and precisely adjusted to pH 7 by NaHCO3 addition. The solution is extracted with ethyl acetate, the extract is dried with Na2SO4 and subsequently mixed with HCl-containing ether. One evaporates, stirs with ether, filters off with suction and dries. Yield 2.3 g (79% of theory) of hydrochloride; m.p. 174°–176° C. (water).

In analogous manner are prepared:

a) 1-[3-[2-(4-bromophenylsulphonylamino)-ethyl]-phenoxy]-3-aminopropane via the step:

1. 1-[3-[2-(4-bromophenylsulphonylamino)-ethyl]-phenoxy]-3-(N-phthalimido)-propane
   (from 4-bromobenzene-sulphochloride and 1-[3-(2-aminoethyl)-phenoxy]-3-(N-phthalimido)-propane).
   Yield 84% of theory; m.p. 105°–107° C. (ethanol)
2. Title compound
   Yield 60% of theory of hydrochloride with the m.p. 174°–175° C. (water)
b) 1-[3-[2-(3-trifluoromethylphenylsulphonylamino)-ethyl]-phenoxy]-3-aminopropane
   Yield 68% of theory of hydrochloride with the m.p. 151°–153° C. (water) via the step:
   1-[3-[2-(3-trifluoromethylphenylsulphonylamino)-ethyl]-phenoxy]-3-(N-phthalimido)-propane
   (from 3-trifluoromethylbenzyl-sulphochloride and 1-[3-(2-aminoethyl)-phenoxy]-3-(naphthylimido)-propane
   Yield 82% of theory; colourless oil.

Example 10

1-[3-[2-(4-Methylphenylsulphonylamino)-ethyl]-phenoxy]-2-aminoethane

1.

3-[2-(4-Methylphenylsulphonylamino)-ethyl]-phenoxyacetic acid benzylamide

To a 40° C. warm mixture of 10.0 g (28.6 mmol) 3-[2-(4-methylphenylsulphonylamino)-ethyl]-phenoxyacetic acid and 100 ml abs. THF one adds 4.64 g (28.6 mmol) carbonyl-bisimidazole and allows to react for 10 min. 0.4 g (28.6 mmol) p-nitrophenol are then added thereto. After 10 min. one adds thereto 3.1 g (28.6 mmol) benzylamine and stirs for two hrs. at 60° C. Subsequently, THF is distilled off, the residue mixed with ice and dil. HCl and shaken out with methylene chloride. One extracts the organic phase twice with NaHCO3 solution and once with water. After drying with MgSO4, it is evaporated and recrystallised (ethanol). Yield 10.2 g (81% of theory); m.p. 118°–120° C.

2.

1-[3-[2-(4-Methylphenylsulphonylamino)-ethyl]-phenoxy]-2-(benzylamino)-ethane

To a mixture of 200 ml abs. THF and 1.65 g (40 mmol) LiAlH4 one adds dropwise a solution of 100 ml abs. THF and 9.5 g (20 mmol) of the amide obtained according to 1. and now allows to boil gently for 4 hrs. It is then cooled and decomposed with ice and NaHCO3 solution. One filters off with suction, extracts the filter cake several times with hot ethyl acetate and dries the combined organic phases with MgSO4. They are then evaporated. One takes up the evaporation residue in ethyl acetate and adds HCl-containing ether to the solution. The precipitated hydrochloride is filtered off with suction and recrystallised from ethanol. Yield 3.9 g (39% of theory) of hydrochloride; m.p. 154°–156° C.

3. Title Compound

One hydrogenates a mixture of 3.5 g (7.6 mmol) of the benzylamino compound obtained according to 2., 50 ml methanol and 0.3 g of 10 percent palladium-charcoal for 48 hrs. at room temperature and normal pressure, subsequently filters off with suction, adds to the filtrate some HCl-containing ether and evaporates. After stirring with ether and drying, 2.28 g (81% of theory) of hydrochloride; m.p. 128°–130° C.

Example 11

N-[2-[3-[2-(4-Chlorophenylsulphonylamino)-ethyl]-phenoxy]-ethyl]-glycine

1.

N-[2-[3-[2-(4-Chlorophenylsulphonylamino)-ethyl]-phenoxy]-ethyl]-glycine ethyl ester One stirs a suspension of 5.0 g (12.8 mmol) 1-[3-[2-(4-chlorophenylsulphonylamino)-ethyl]-phenoxy]-2-aminoethane hydrochloride, 100 ml methylene chloride and 3.88 g. (38.3 mmol) triethylamine for 30 min, adds thereto 4.70 g (28 mmol) bromoacetic acid ethyl ester and allows to stir for six hrs. at room temperature. Soda solution is then added thereto and the organic phase separated off. One dries with MgSO4 and evaporates. After separation by means of preparative HPLC (Europrep RP 18, methanol 65/buffer 7.8, 35 vol.), one obtains 2.5 g (41% of theory) of colourless oil.

2. Title Compound

A mixture of 2.5 g (5.24 mmol) of the ester obtained according to 1. in the form of the hydrochloride, 10 ml 2N NaOH and 10 ml of ethanol is stirred for one hr. at 50° C. One then distils off the ethanol, dilutes the residue with water and shakes out twice with ethyl acetate. The aqueous phase is acidifed with dil. HCl, the crystalline hydrochloride thereby precipitating out. After suction filtration, washing with water and drying, 2.2 g (94% of theory) of hydrochloride with the m.p. 205°–207° C. (aq. ethanol).

Example 12

1-[3-[2-(4-Chlorophenylsulphonylamino)-ethyl]-phenyl]-2-aminoethane 1. 1,3-Bis-(2-aminoethyl)-benzene A mixture of 25.0 g (0.16 mmol) meta-xylylene dicyanide, 300 ml ethanol and 50 ml conc. NH3 is hydrogenated in the presence of Raney nickel for 5 hrs. at 100° C. and 150 bar. One then filters off with suction and evaporates. The residue is dissolved in ether, the solution is clarified with active carbon and finally mixed with HCl-containing ether, whereby the dihydrochloride precipitates out. One filters off with suction, washes with ether and dries. Yield 23.2 g (61% of theory) of dihydrochloride with the m.p. 282°–286° C.

2. Title Compound

To a mixture of 6.0 g (25.2 mmol) of the dihydrochloride obtained according to 1. and 5.4 g (25.2 mmol) 4-chlorobenzene sulphochloride in 500 ml methanol are slowly added dropwise at −50° C. and with vigorous stirring 25.2 mol 2N NaOH (50.4 mmol). One then stirs for a further 30 min, whereby one allows to come to room temperature, mixes with soda solution and shakes out with ethyl acetate. The ethyl acetate phase is dried (Na2SO4) and evaporated. For purification, it is separated via a middle pressure chromatography column: RP 18, methanol:buffer, pH 7.8=7.3 vol. Yield 3.4 g (40% of theory); m.p. 194°–195° C. (methanol).

As by-product, there is obtained some 1,3-bis-[2-(4-chlorophenylsulphonylamino)-ethyl]-benzene with the m.p. 135°–136° C.

Experimental Report

1. TX-antagonistic action on the isolated rat sorts ring pre-contracted with U 46619

Method

The isolated rat sorts freed from surrounding connective tissue is cut up into equally wide rings and superinfused in a 10 ml organ bath with Krebs-Hanseleit buffer at 37° C. After about 45 min., equilibration time, the sorts rings are precontracted with 0.3 μmol/l U 46619, a stable analogue of the prostaglandin endoperoxide $PGH_2$ (Upjohn & Co., Kalamazoo, USA). U 46619 was characterised as selective thromboxane mimetic (Coleman et al., Brit. J. Pharmacol. 68, 127P, 1980). As soon as a stable plateau is reached (after about 15 min.), the test substance is added cumulatively directly into the organ bath to the aorta ring, beginning with 10 nmol/l, until either an end concentration of 100 μmol/l is reached or the contraction is completely antagonised. There is calculated the particular percentage inhibition of the contraction by the test substance. From the concentration-action curves is determined the $IC_{50}$, i.e. the half maximum inhibiting concentration.

2. Prevention of the U 46619-caused lung embolism

Male NMRI mice of about 25 g body weight are used. The test substance is suspended in 1% methyl cellulose solution and administered to the experimental animals by means of a stomach probe. The provocation test consists in that a dose lethal for the control animals (800–1000 μg/kg) of the thromboxane mimetic (U 46619 of the firm Upjohn) is rapidly injected into the tail vein. The period of the specific antagonistic action is tested in that the animals are pre-treated with 1 mg/kg of the various test substances and the injection of U 46619 takes place after 4 h. The survival rate indicates what percent of the animals used survive the injection of the thromboxane mimetic.

3. Inhibition of the U 46619-induced bronchospasm of the anaesthetised guinea pig

Method

Guinea pigs are anaesthetised with narcoren and provided with a jugular vein catheter and a tracheal canula. The animals are mechanically respirated with atmospheric air with 1 ml/100 g body weight. The tracheal canula is connected via a three-way stopcock with a Stathem pressure element which takes up the pressure resulting by the contraction of the smooth musculature in the trachea and passes on to a recorder via a measuring bridge. After achievement of a constant basal tonus, the animals receive 10 μg/kg U 46619 i.v. administered via the jugular vein catheter. The dose induces a rapidly increasing bronchospasm which, after about 10 minutes, again subsides and is very readily reproducable. After 15 minutes follows a second administration of 10 μg/kg U 46619, in the course of which, after 5 minutes, the test substance is given i.v. in various doses. After a further 15 minutes, the same dose of U 46619 is again injected. The areas under the curve over 10 min of the administration 1 and 3 are determined planimetrically on a Kontron-Videoplan unit and the bronchospasm after administration 3 calculated in percentage of the bronchospasm after administration 1. The $ID_{50}$ of the test substance can be determined from the quotients.

Table

| substance (Ex. No.) | survival rate of mouse 1 mg/kg after 4 h in % | $IC_{50}$ of the pre-contracted isolated rat aortas (μmol/l) | $ID_{50}$ of U46619-induced bronchospasm of the guinea pig (mg/kg) |
|---|---|---|---|
| Ex. 1 r | 90 | 1.0 | 0.02 |
| Ex. 1 g | 100 | 1.6 | 0.04 |
| Ex. 2 a | 100 | 1.8 | 0.01 |
| Ex. 1 d | 100 | 3.4 | 0.50 |
| Ex. 1 f | 100 | 1.6 | 0.02 |
| Ex. 4 | 100 | 0.34 | 0.01 |
| Ex. 5 | 100 | 0.10 | 0.05 |
| Ex. 4 m | 100 | 3.00 | 0.05 |
| Ex. 4 s | 90 | 2.6 | 0.10 |

We claim:

1. A compound of the general formula I

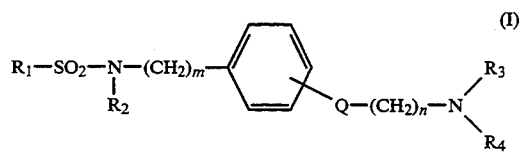

in which $R_1$ is an aryl, aralkyl or an aralkenyl group, the aryl radical of which is unsubstituted or substituted one or more times by halogen, cyano, alkyl, trifluoromethyl, alkoxy, alkylthio, trifluoromethoxy, hydroxyl or carboxyl, m a whole number of 2, n a whole number from 2 to 5, $R_2$ is hydrogen, Q is a bond or an oxygen atom, $R_3$ is hydrogen or a $C_1$-$C_4$-alkyl group which is unsubstituted or terminally substituted by a carboxyl or a hydroxy group and $R_4$ is hydrogen, a lower alkyl group with 1-4 C-atoms which is unsubstituted or terminally substituted by carboxyl or hydroxyl, an unsubstituted or substituted phenyl, pyridinyl, pyrimidinyl, cycloalkyl or acyl group or a group

in which $R_5$ is a straight-chained or branched alkyl chain with 1-4 C-atoms which is unsubstituted or terminally substituted by carboxyl, alkoxycarbonyl, aminocarbonyl, hydroxyl, mercapto, alkylthio or imidazolyl and Y is a carboxyl, an alkoxycarbonyl, aminocarbonyl or cyano, formyl, hydroxymethyl, aminomethyl or an ortho ester group, wherein $R_3$ and $R_4$ can also together form a 5- or 6-membered saturated or unsaturated unsubstituted or substituted heterocycle with 1-4 heteroatoms which is not annellated or is annellated with further ring compounds via one or more bonds, or a physiologically compatible salt, ester or amide thereof with the proviso that $R_3$ and $R_4$ are not both lower alkyl groups.

2. Compound of claim 1, wherein the compound is 1-[3-[2-(4-chlorophenylsulphonylamino)-ethyl]-phenoxy]-2-aminoethane.

3. Compound of claim 1, wherein the compound is 4-[2-(4-chlorophenylsulphonylamino)-ethyl]-phenoxyacetic acid (3-pyridyl)-amide.

4. Compound of claim 1, wherein the compound is 3-[2-(4-chlorophenylsulphonylamino)-ethyl]-phenoxy-acetic acid ethylamide.

5. A pharmaceutical composition suitable for producing a thromboxane-antagonistic action, comprising a thromboxane-antagonistic-effective amount of a compound of claim 1 and a pharmaceutically acceptable carrier thereof.

6. Composition of claim 5, wherein said compound is 4-[2-(4-chlorophenylsulphonylamino)-ethyl]-phenoxy-acetic acid (3-pyridyl)-amide.

7. Composition of claim 5, wherein said compound is 3-[2-(4-chlorophenylsulphonylamino)-ethyl]-phenoxy-acetic acid ethylamide.

8. A method of producing a thromboxane antagonistic effect in a patient in need of such effect, said method comprising administering to the patient a thromboxane-antagonistic-effective amount of a compound of claim 1.

9. Method of claim 8, wherein said compound is 4-[2-(4-chlorophenylsulphonylamino)-ethyl]-phenoxy-acetic acid (3-pyridyl)-amide.

10. Method of claim 8, wherein said compound is 3-[2-(4-chlorophenylsulphonylamino)-ethyl]-phenoxy-acetic acid ethylamide.

11. Compound of claim 1, wherein the compound is 1-[4-[2-(4-chlorophenylsulphonylamino)-ethyl]-phenyl]-2-aminoethane.

12. Composition of claim 5, wherein said compound is 1-[3-[2-(4-chlorophenylsulphonylamino-ethyl]-phenoxy]-2-aminoethane.

13. Composition of claim 5, wherein said compound is 1-[4-[2-(4-chlorophenylsulphonylamino)-ethyl]-phenyl]-2-aminoethane.

14. Method of claim 8, wherein said compound is 1-[3-[2-(4-chlorophenylsulphonylamino)-ethyl]-phenoxy]-2-aminoethane.

15. Method of claim 8, wherein said compound is 1-[4-[2-(4-chlorophenylsulphonylamino)-ethyl]-phenyl]-2-aminoethane.

* * * * *